United States Patent
Pandey et al.

(10) Patent No.: US 12,350,269 B2
(45) Date of Patent: *Jul. 8, 2025

(54) CERDULATINIB FOR THE TREATMENT OF B-CELL MALIGNANCIES

(71) Applicant: Alexion Pharmaceuticals, Inc., Boston, MA (US)

(72) Inventors: Anjali Pandey, Fremont, CA (US); Gregory Coffey, Emerald Hills, CA (US); Janet Leeds, South San Francisco, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 646 days.

This patent is subject to a terminal disclaimer.

(21) Appl. No.: 17/316,530

(22) Filed: May 10, 2021

(65) Prior Publication Data

US 2022/0096471 A1 Mar. 31, 2022

Related U.S. Application Data

(63) Continuation of application No. 15/578,190, filed as application No. PCT/US2016/034861 on May 27, 2016, now abandoned.
(Continued)

(51) Int. Cl.
*A61K 31/506* (2006.01)
*A61K 31/497* (2006.01)
(Continued)

(52) U.S. Cl.
CPC .......... *A61K 31/506* (2013.01); *A61K 31/497* (2013.01); *A61K 45/06* (2013.01); *A61P 35/02* (2018.01)

(58) Field of Classification Search
None
See application file for complete search history.

(56) References Cited

U.S. PATENT DOCUMENTS

| | | |
|---|---|---|
| 4,673,747 A | 6/1987 | Nohara et al. |
| 5,760,032 A | 6/1998 | Kitajima et al. |
| | (Continued) | |

FOREIGN PATENT DOCUMENTS

| | | |
|---|---|---|
| EP | 1518855 | 3/2005 |
| WO | WO 2008/009458 | 1/2008 |
| | (Continued) | |

OTHER PUBLICATIONS

Friedberg et al., Blood. Apr. 1, 2010;115(13):2578-2785 (Year: 2010).*

(Continued)

*Primary Examiner* — Jeffrey S Lundgren
*Assistant Examiner* — Anthony Joseph Seitz
(74) *Attorney, Agent, or Firm* — Sheppard Mullin Richter & Hampton LLP

(57) ABSTRACT

Provided herein are compositions and methods for treating a relapsed or refractory hematologic cancer in a human patient in need thereof. The methods entail administering to the patient a daily dose of about 10 mg to about 75 mg of cerdulatinib or a pharmaceutically acceptable salt thereof, wherein the patients suffer one or more of a B-cell malignancy, chronic lymphocytic leukemia (CLL), follicular lymphoma (FL), diffuse large B-cell lymphoma (DLBCL) or other transformed FL and/or have relapsed or not responded to a prior chemotherapy.

10 Claims, 7 Drawing Sheets

Related U.S. Application Data

(60) Provisional application No. 62/263,582, filed on Dec. 4, 2015, provisional application No. 62/168,530, filed on May 29, 2015.

(51) Int. Cl.
 *A61K 45/06* (2006.01)
 *A61P 35/02* (2006.01)

(56) References Cited

U.S. PATENT DOCUMENTS

| | | | |
|---|---|---|---|
| 6,627,626 | B2 | 9/2003 | Minich et al. |
| 7,449,456 | B2 | 11/2008 | Nagashima et al. |
| 7,557,210 | B2 | 7/2009 | Singh et al. |
| 8,012,959 | B2 | 9/2011 | Nagashima et al. |
| 8,138,339 | B2 | 3/2012 | Bauer et al. |
| 8,501,944 | B2 | 8/2013 | Bauer et al. |
| 8,937,070 | B2 | 1/2015 | Bauer et al. |
| 9,676,756 | B2 | 6/2017 | Bauer et al. |
| 9,868,729 | B2 | 1/2018 | Bauer et al. |
| 10,736,895 | B2 * | 8/2020 | Coffey .......... A61K 31/519 |
| 11,446,300 | B2 * | 9/2022 | Coffey .......... A61K 31/635 |
| 2011/0294749 | A1 | 12/2011 | Nagashima et al. |
| 2012/0129867 | A1 | 5/2012 | Bauer et al. |
| 2013/0040973 | A1 | 2/2013 | Vannucchi et al. |
| 2013/0237493 | A1 * | 9/2013 | Sinha .......... A61K 31/506 514/48 |
| 2014/0371241 | A1 | 12/2014 | Buggy et al. |
| 2017/0042896 | A1 | 2/2017 | Coffey et al. |
| 2018/0353506 | A1 | 12/2018 | Coffey et al. |

FOREIGN PATENT DOCUMENTS

| | | |
|---|---|---|
| WO | WO 2009/145856 | 12/2009 |
| WO | WO 2010/129802 | 11/2010 |
| WO | WO 2012/045020 | 4/2012 |
| WO | WO 2014/018567 | 1/2014 |
| WO | WO 2016/040858 | 3/2016 |
| WO | WO 2017/027829 | 2/2017 |
| WO | WO 2017/096303 | 6/2017 |

OTHER PUBLICATIONS

Zahreddine et al., Front Pharmacol. Mar. 14, 2013;4:28 (Year: 2013).*
Quiroga et al., B-cell antigen receptor signaling enhances chronic lymphocytic leukemia cell migration and survival: specific targeting with a novel spleen tyrosine kinase inhibitor, R406, Blood, vol. 114, Issue 5, 2009, pp. 1029-1037 (Year: 2009).*
U.S. Appl. No. 62/342,755, filed May 27, 2016, Coffey et al.
U.S. Appl. No. 62/371,145, filed Aug. 4, 2016, Coffey er al.
U.S. Appl. No. 62/667,226, filed May 4, 2018, Pandey et al.
U.S. Appl. No. 62/667,235, filed May 4, 2018, Pandey et al.
U.S. Appl. No. 63/003,096, filed Mar. 31, 2020, Conley et al.
Akinleye et al. Ibrutinib and indolent B-cell lymphomas. Clin Lymphoma Myeloma Leuk. Aug. 2014;14(4):253-60.
Bartlett et al. Ibrutinib Monotherapy in Relapsed/Refractory Follicular Lymphoma (FL): Preliminary Results of a Phase 2 Consortium (P2C) Trial. Blood (2014) vol. 124, 800.
Blunt et al., "The dual Syk/JAK inhibitor cerdulatinib antagonises B-cell receptor and microenvironmental signaling in chronic lymphocytic leukemia.", Clinical Cancer Research : An Official Journal of the American Association for Cancer Research Oct. 3, 2016, Oct. 3, 2016 (Oct. 3, 2016), XP002767268, ISSN: 1078-0432.
Blunt et al., "The Syk\Jak Inhibitor Cerdulatinib (PRT062070) Shows Promising Preclinical Activity in Chronic Lymphocytic Leukemia By Antagonising B Cell Receptor and Microenvironmental Signalling", Blood, American Society of Hematology, US, vol. 126, No. 23, Dec. 3, 2015 (Dec. 3, 2015), XP009193491, ISSN: 0006-4971.
Cheng et al., "Functional characterization of $BTK^{C481S}$ mutation that confers irbrutinib resistance: exploration of alternative kinase inhibitors", Leukemia (201) 29, 895-900.
Coffey et al., "The Novel Kinase Inhibitor PRT062070 (Cerdulatinib) Demonstrates Efficacy in Models of Autoimmunity and B-Cell Cancer", The Journal of Pharmacology and Experimental Therapeutics, 2014, vol. 351, No. 3, pp. 538-548.
Hamlin et al., "Clinical and Correlative Results of a Phase 1 Study of Cerdulatinib (PRT062070) a Dual SYK/JAK Inhibitor in Patients with Relapsed/Refractory B Cell Malignancies", Blood, vol. 126, No. 23, Dec. 3, 2015 (Dec. 3, 2015), XP009193500, & 57th Annual Meeting of the American-Society-of Hematology; Orlando, FL, USA; Dec. 5-8, 2015.
How is Multiple Myeloma Staged? printed Aug. 17, 2017. https://www.cancer.org/cancer/multiple-myeloma/detection-diagnosisstaging/staging.html.
International Search Report and Written Opinion for PCT/US2016/034861 dated Sep. 7, 2016, 8 pages.
International Search Report and Written Opinion for PCT/US2016/046862 dated Oct. 31, 2016, 9 pages.
International Search Report and Written Opinion for PCT/US2016/064824 dated Jul. 5, 2017, 14 pages.
Ma et al., "Cerdulatinib, a novel dual SYK/JAK kinase inhibitor, has broad anti-tumor activity in both ABC and GCB types of diffuse large B cell lymphoma.", Oncotarget, vol. 6, No. 41, Nov. 5, 2015 (Nov. 5, 2015), pp. 43881-43896, XP002767267, ISSN: 1949-2553.
Patel et al., "A Phase I Open-Label, Multi-Dose Escalation Study of the Dual Syk/Jak Inhibitor PRT062070 (Cerdulatinib) in Patients with Relapsed/Refractory B Cell Malignancies", Blood, vol. 124, No. 21, Dec. 2014 (Dec. 2014), XP009193499, & 56th Annual Meeting of the American-Society-of-Hematology; San Francisco, CA, USA; Dec. 6 -9, 2014.
Reagan-Shaw et al., "Dose translation from animal to human studies revisited", FASEB Journal, 2007, vol. 22, pp. 659-661.
Ross et al. Comprehensive analysis analysis number and allele status identifies multiple chromosome defects underlying follicular lymphoma pathogenesis. Clin Cancer Res. Aug. 15, 2007;13(16):4777-85.
Scuto et al., "The novel JAK inhibitor AZD1480 blocks STAT3 and FGFR3 signaling, resulting in suppression of human myeloma cell growth and survival", Leukemia, 2011, 25(3), pp. 538-550.
Shimura et al., "RSK2ser227 at N-Terminal Kinase Domain is a Potential Therapeutic Target for Multiple Myeloma", Molecular Cancer Therapeutics, 2012, 11(12), pp. 2600-2609.
Stedman's Medical Dictionary 27th Edition, 2000, pp. 865-866.
Wang et al., "SYK and STAT3 are active in diffuse large B-cell Lymphoma: Activity of cerdulatinib, a dual SYK/JAK inhibitor", Blood, 2014, 124:926, 6 pages.
Zahreddine et al. Mechanisms and insights into druf resistance in cancer. Front Pharmacol. Mar. 14, 2013;4:28.
Zhang et al., "Mechanisms of ibrutinib resistance in chronic lymphocytic leukaemia and non-Hodgkin lymphoma", British Journal of Haematology, 2015, 170, 445-456, 12 pages.
Hamlin, et al. Efficacy and safety of the dual SYK/JAK inhibitor cerdulatinib in patients with relapsed or refractory B-cell malignancies: Results of a phase I study. American journal of hematology 94, No. 4 (2019): E90-E93.

* cited by examiner

CERDULATINIB FOR THE TREATMENT OF B-CELL MALIGNANCIES

CROSS-REFERENCE TO RELATED APPLICATIONS

This application is a continuation of U.S. application Ser. No. 15/578,190, filed Nov. 29, 2017, which is a United States National Stage Application under 35 U.S.C. § 371 of International Application No. PCT/US2016/034861, filed May 27, 2016, which application claims the benefit under 35 U.S.C. § 119 (e) of U.S. Provisional Patent Application Nos. 62/168,530, filed on May 29, 2015, and 62/263,582, filed on Dec. 4, 2015, each of which is hereby incorporated by reference in its entirety.

FIELD

The present disclosure relates generally to methods of using cerdulatinib for treating hematological cancers, including B-cell malignancies and relapsed or refractory hematological cancers.

BACKGROUND

Tumors of the hematopoietic and lymphoid tissues or hematopoietic and lymphoid malignancies are tumors that affect the blood, bone marrow, lymph, and lymphatic system. As those elements are all intimately connected through both the circulatory system and the immune system, a disease affecting one will often affect the others as well, making myeloproliferation and lymphoproliferation (and thus the leukemias and the lymphomas) closely related and often overlapping problems.

Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

B-cell lymphomas are types of lymphoma affecting B cells. Lymphomas are "blood cancers" in the lymph nodes. B-cell lymphomas include both Hodgkin's lymphomas and most non-Hodgkin lymphomas.

Follicular lymphoma (FL) is a type of blood cancer. It is the most common of the indolent (slow-growing) non-Hodgkin's lymphomas, and the second-most-common form of non-Hodgkin's lymphomas overall. It is defined as a lymphoma of follicle center B-cells (centrocytes and centroblasts), which has at least a partially follicular pattern.

B-cell chronic lymphocytic leukemia (B-CLL), also known as chronic lymphoid leukemia (CLL), is the most common type of leukemia (a type of cancer of the white blood cells) in adults. CLL affects B cell lymphocytes, which originate in the bone marrow, develop in the lymph nodes, and normally fight infection by producing antibodies. CLL is a stage of small lymphocytic lymphoma (SLL), a type of B-cell lymphoma, which presents primarily in the lymph nodes. CLL and SLL are considered the same underlying disease, just with different appearances.

Diffuse large B-cell lymphoma (DLBCL or DLBL) is a cancer of B cells, a type of white blood cell responsible for producing antibodies. Diffuse large B-cell lymphoma encompasses a biologically and clinically diverse set of diseases, many of which cannot be separated from one another by well-defined and widely accepted criteria.

B cell receptor (BCR) mediated signalling is required for chronic lymphocytic leukemia (CLL) pathogenesis and drugs which target kinases within the BCR signalling complex are revolutionising the treatment of this disease.

Some chemotherapeutic agents employed in CLL therapy include ibrutinib (IMBRUVICA®), which targets BTK and idelalisib (ZYDELIG®), which targets P13Kδ. However these compounds suppress the disease and are not typically curative. Additionally, CLL patients may develop resistance to these chemotherapeutic agents either via mutations in BTK or downstream signalling proteins, or other mechanisms.

Current treatment options for patients who fail standard therapies for CLL, SLL, DLBCL, and FL are limited. Accordingly, there is a need for new therapies for hematological malignancies.

SUMMARY

Provided herein are methods of treating a hematologic cancer, or B-cell malignancies, in a human patient in need thereof, comprising administering to the patient a daily dose of about 10 mg to about 75 mg of cerdulatinib or a pharmaceutically acceptable salt thereof.

Also provided herein are methods for treating a relapsed or refractory hematologic cancer in a patient in need thereof, comprising administering to the patient an effective amount of cerdulatinib, or a pharmaceutically acceptable salt thereof.

Some embodiments provide for methods of treating a relapsed or refractory hematologic cancer in a patient in need thereof, comprising administering to the patient an effective amount of cerdulatinib, or a pharmaceutically acceptable salt thereof, wherein:

the patient has a mutation linked to relapse and/or a resistance to a drug for treating a hematological cancer; and the effective amount of cerdulatinib, or a pharmaceutically acceptable salt thereof, is a daily dose of about 30 mg to about 80 mg of cerdulatinib.

In some embodiments, the hematologic cancer is Chronic Lymphocytic Leukemia (CLL), Small Lymphocytic Lymphoma (SLL), Follicular Lymphoma (FL), transformed Follicular Lymphoma (tFL), Diffuse Large B-cell Lymphoma (DLBCL), or Mantle Cell Lymphoma (MCL).

In some embodiments, the patient in need thereof is a patient exhibiting drug resistance to and/or a relapsed for a hematological cancer for a number of reasons. For example, the patient may have a mutation linked to relapse and/or a resistance to a drug for treating a hematological cancer. For example, the patient may have a del17p mutation, a P53 mutation, an ATM mutation, a STAT mutation, a STAT 6 mutation, a C481S STAT6 mutation, a mutation associated with the NOTCH pathway, a mutation associated with the Caderin pathway, or a combination thereof. According to some embodiments, the patient does not have a mutation in all of P53, BTK, and EP300.

DETAILED DESCRIPTION

1. Definitions

Figure 1:
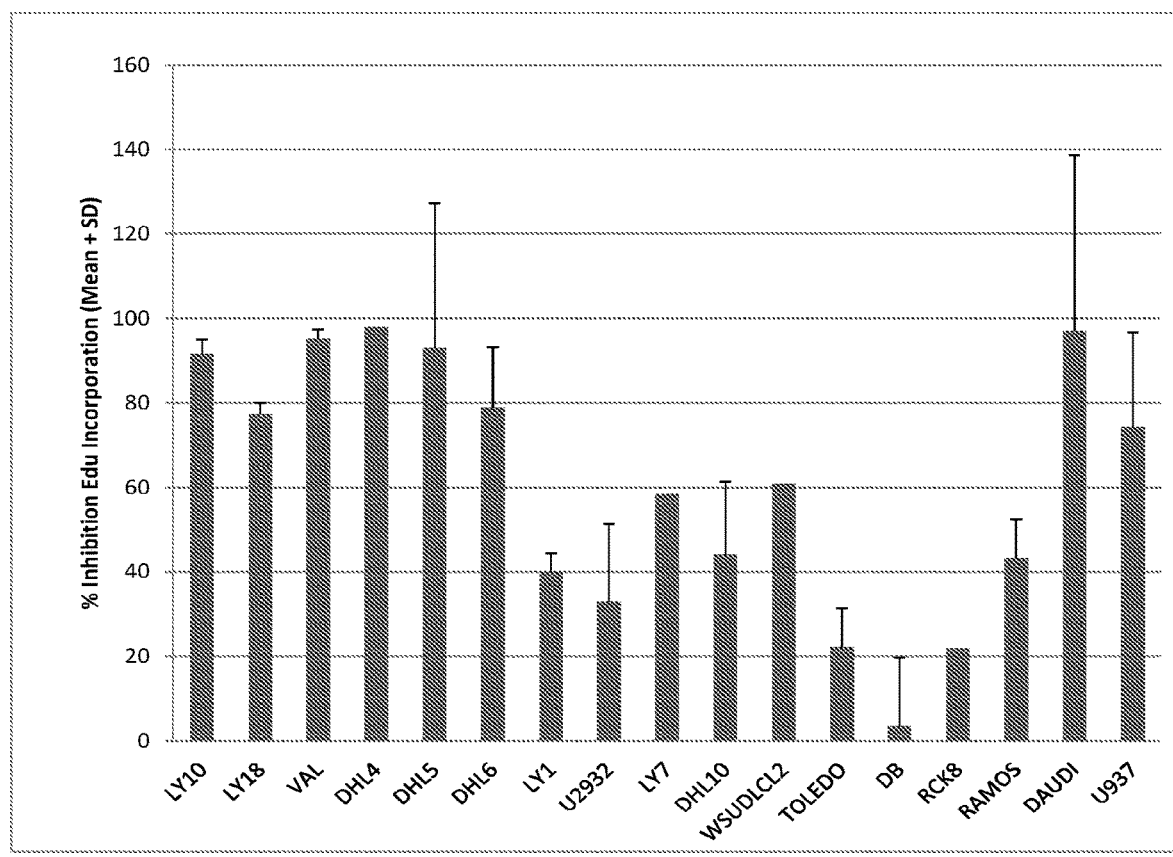
FIG. 1 provides a bar graph that depicts inhibition of Edu incorporation by FACS analysis in a variety of DLBCL cell lines at 2 μM of cerdulatinib at 72 hours.

Unless defined otherwise, all technical and scientific terms used herein have the same meaning as commonly understood by one of ordinary skill in the art to which this disclosure belongs. As used herein the following terms have the following meanings.

It must be noted that as used herein and in the appended claims, the singular forms "a", "an", and "the" include plural referents unless the context clearly dictates otherwise. Thus, for example, reference to "an agent" includes a plurality of agents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "pharmaceutically acceptable salt" refers to any acid or base addition salt whose counter-ions are non-toxic to the patient in pharmaceutical doses of the salts. A host of pharmaceutically acceptable salts are well known in the pharmaceutical field. If pharmaceutically acceptable salts of the compounds of this disclosure are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

"Prodrug"s of cerdulatinib or other compounds described herein are also encompassed and are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH₃ comprises the progroup —C(O)CH₃.

A wide variety of progroups, as well as the resultant promoieties, suitable for masking functional groups in the compounds described herein to yield prodrugs are well-known in the art. For example, an amino functional group may be masked as an amide, carbamate, imine, urea, phosphenyl, phosphoryl or sulfenyl promoiety, which may be hydrolyzed in vivo to provide the amino group. The disclosure includes those esters and acyl groups known in the art for modifying the solubility or hydrolysis characteristics for use as sustained-release or prodrug formulations. Other specific examples of suitable progroups and their respective promoieties will be apparent to those of skill in the art.

As used herein, an "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein includes both one and more than one such carrier or excipient.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Patient" refers to human and non-human animals, especially mammals. Examples of patients include, but are not limited to, humans, cows, dogs, cats, goats, sheep, pigs and rabbits.

The terms "treat," "treating," "treatment," and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments as described herein may be applied preventively, prophylactically, palliatively or remedially.

The terms "prevent," "preventing," "prevention," and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or requiring a disorder or condition or one or more of its attendant symptoms.

In the present context, the term "therapeutically effective" or "effective amount" indicates that a compound or material or amount of the compound or material when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. The dosage can be conveniently administered, e.g., in divided doses up to four times a day or in sustained-release form.

As used herein, "daily dose" refers to a total amount of a therapeutic substance that is to be taken within 24 hours.

The methods and compositions described herein will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

2. Methods of Use

Malignant B cells receive survival signals that originate from a tumor itself as well as from non-tumor cells residing in the microenvironment. The B cell antigen receptor (BCR) and cytokine receptors contribute to survival.

Subsets of B cell lymphomas demonstrate a reliance on BCR and/or cytokine JAK/STAT signaling for survival. SYK is positioned upstream of BTK, PI3Kδ, and PLCγ2 on the BCR signaling pathway, making it a potential therapeutic target. Additional survival support appears to be mediated by cytokine-induced JAK/STAT pathways, which can be activated by tumor autocrine signaling loops, or by pro-inflammatory cytokines originating from non-tumor infiltrating leukocytes present in the tumor microenvironment.

Increased serum concentrations of several cytokines are observed in CLL and non-Hodgkin's lymphoma ("NHL"), and predict a more aggressive disease progression. The source of these cytokines may be derived from the tumor itself in an autocrine stimulation fashion, or from non-tumor leukocytes which have mounted an ineffective immune response within the tumor microenvironment. Experimentally, IL4 has been shown to promote the survival of CLL B-cells in culture and protect them from death by treatment with fludarabine and chlorambucil. The mechanism underlying this survival support appears to be cytokine-induced up-regulation of BCL2 family members.

The importance of B cell receptor (BCR) mediated signaling in the pathogenesis of chronic lymphocytic leukaemia (CLL) has become even more apparent in recent years, and drugs which target kinases within the BCR signaling complex are revolutionizing the treatment of this disease. Recently approved agents for relapsed/refractory CLL include ibrutinib (BTK inhibitor) and idelalisib (PI3Kδ inhibitor). To date, these compounds have not proved curative, which may in part be mediated by signals from the tumor. Importantly, a proportion of patients are developing resistance to these new agents, either through mutations in BTK or PLCγ for ibrutinib or because of as yet unknown mechanisms. Spleen tyrosine kinase (SYK) belongs to the SYK/ZAP70 family of non-receptor kinases and plays a central role in the transmission of activating signals downstream of the BCR, chemokine and integrin receptors within B cells, and remains an intriguing target for the treatment of certain B cell malignancies and autoimmune disease.

CLL cells are dependent upon signals from various cells constituting the microenvironment. IL-4 signals in lymphocytes are derived predominantly through the type 1 IL-4 receptor (IL-4R) via Janus protein tyrosine kinases JAK1 and JAK3 resulting in phosphorylation of STAT6 (pSTAT6).

Current treatment options for patients who fail standard therapies for chronic lymphocytic leukemia (CLL), small lymphocytic lymphoma (SLL), and follicular lymphoma (FL) are limited.

Provided herein are methods of treating a hematological cancer by administration of cerdulatinib. Cerdulatinib is a small molecule, ATP-competitive, reversible inhibitor of both SYK and JAK family members. Cerdulatinib, which has been described previously (see, e.g., U.S. Pat. No. 8,138,339), has a chemical name 4-(cyclopropylamino)-2-(4-(4-(ethylsulfonyl)piperazin-1-yl)phenylamino)pyrimidine-5-carboxamide, and has the formula:

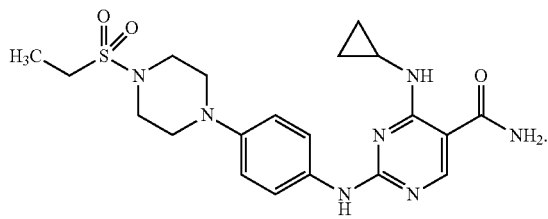 [SMILES: CCS(=O)(=O)N1CCN(c2ccc(Nc3ncc(C(N)=O)c(NC4CC4)n3)cc2)CC1]

In embodiments described herein, cerdulatinib may also refer to a pharmaceutically acceptable salt or prodrug thereof.

It is contemplated that cerdulatinib may be useful for heavily pre-treated patients and/or relapse/refractory hematological cancers, including but not limited to CLL, FL, NHL, and DLBCL. Cerdulatinib also induces apoptosis in primary CLL, with preferential activity in cases of poor prognosis such as unmutated IGHV, high CD49d, ZAP-70, or surface IgM expression.

Provided herein are methods of treating a hematologic cancer in a human patient in need thereof, comprising administering to the patient a daily dose of about 10 mg to about 75 mg of cerdulatinib, or a pharmaceutically acceptable salt thereof, or a pharmaceutical composition comprising a daily dose of about 10 mg to about 75 mg of cerdulatinib, or a pharmaceutically acceptable salt thereof, and at least one pharmaceutically acceptable excipient or carrier.

Also provided herein are methods for treating a relapsed or refractory hematologic cancer in a patient in need thereof, comprising administering to the patient an effective amount of cerdulatinib, or a pharmaceutically acceptable salt thereof, or a pharmaceutical composition comprising a daily dose of about 10 mg to about 75 mg of cerdulatinib, or a pharmaceutically acceptable salt thereof, and at least one pharmaceutically acceptable excipient or carrier.

Some embodiments provide for methods of treating a relapsed or refractory hematologic cancer in a patient in need thereof, comprising administering to the patient an effective amount of cerdulatinib, or a pharmaceutically acceptable salt thereof, or a pharmaceutical composition comprising an effective amount of cerdulatinib, or a pharmaceutically acceptable salt thereof, and at least one pharmaceutically acceptable excipient or carrier, wherein:

the effective amount of cerdulatinib, or a pharmaceutically acceptable salt thereof, is a daily dose of about 30 mg to about 80 mg of cerdulatinib.

Some embodiments provide for methods of treating a relapsed or refractory hematologic cancer in a patient in need thereof, comprising administering to the patient an effective amount of cerdulatinib, or a pharmaceutically acceptable salt thereof, or a pharmaceutical composition comprising an effective amount of cerdulatinib, or a pharmaceutically acceptable salt thereof, and at least one pharmaceutically acceptable excipient or carrier, wherein:

the patient has a mutation linked to relapse and/or a resistance to a drug for treating a hematological cancer; and the effective amount of cerdulatinib, or a pharmaceutically acceptable salt thereof, is a daily dose of about 30 mg to about 80 mg of cerdulatinib.

Some embodiments provided herein are related to methods of treating a patient suffering from one or more of a B-cell non-Hodgkin's lymphoma (NHL), chronic lymphocytic leukemia (CLL), follicular lymphoma (FL), diffuse large B-cell lymphoma (DLBCL) or other transformed FL.

In some embodiments, the patient suffers one or more of B-cell malignancy, chronic lymphocytic leukemia (CLL), follicular lymphoma (FL), or transformed FL.

In some embodiments, the patient suffers from an advanced malignancy.

In some embodiments, the patient has relapsed or not responded to a prior chemotherapy. In some embodiments, the patient has failed at least two prior therapies. In some embodiments, the patient has failed at least one prior therapy.

In some embodiments, the patient has a B cell malignancy. In some embodiments, the methods provided herein are used to treat a hematological cancer such as chronic lymphocytic leukemia (CLL), small lymphocytic lymphoma (SLL), follicular lymphoma (FL), transformed follicular lymphoma (tFL), diffuse large B-cell lymphoma (DLBCL), and/or mantle cell lymphoma (MCL). In some embodiments, the methods provided herein are used to treat a hematological cancer such as non-Hodgkin's lymphoma (NHL), chronic lymphocytic leukemia (CLL), small lymphocytic lymphoma (SLL), follicular lymphoma (FL), transformed follicular lymphoma (tFL), diffuse large B-cell lymphoma (DLBCL), and/or mantle cell lymphoma (MCL).

According to some embodiments, the hematological cancer is CLL. According to some embodiments, the hematological cancer is DLBCL. According to some embodiments, the hematological cancer is FL. According to some embodiments, the hematological cancer is SLL. According to some embodiments, the hematological cancer is NHL. According to some embodiments, the hematological cancer is tFL. According to some embodiments, the hematological cancer is MCL.

Some chemotherapeutic agents suffer from drug resistance in a patient, for example, due to BCR IL-4 mediated signalling and/or BCR activation pathways, which are protective of hematological cancer. According to embodiments of the present disclosure, cerdulatinib can overcome these protective mechanisms, which lead to drug resistance.

In some embodiments, the patient in need thereof is a patient exhibiting drug resistance to, and/or a relapsed for, of a hematological cancer for a number of reasons. For example, the patient may have a mutation linked to relapse and/or a resistance to a drug for treating a hematological cancer. For example, the patient may have a del17p mutation, a P53 mutation, an ATM mutation, a STAT mutation, a STAT 6 mutation, a C481S STAT6 mutation, a mutation associated with the NOTCH pathway, or a mutation associated with the Caderin pathway.

In some embodiments, the patient may have a S86A mutation in STAT.

In some embodiments, the patient may have a del17p mutation, del11q mutation, a P53 mutation, an ATM mutation, a STAT mutation, a STAT 6 mutation, a C481S STAT6 mutation, a mutation associated with the NOTCH pathway, a mutation associated with the Caderin pathway, or a combination thereof.

According to some embodiments, the patient does not have a mutation in each of P53, BTK, and EP300.

In some embodiments, the patient has a MYD88 mutation, a CARD11 mutation, or a A20 mutation. In some embodiments, the patient has high-risk genetic abnormalities including del11q, trisomy 12, and del17p. In some embodiments, the patient has a del17p mutation. In some embodiments, the patient has a del11q mutation.

In some embodiments, the patient has a BTK mutation.

In some embodiments, the patient may have a poor prognosis such as unmutated IGHV, high CD49d, ZAP-70, or surface IgM expression.

In some embodiments, the patient has resistance to a drug, which is not cerdulatinib. Non-limiting examples of these drugs are an anti-CD20 antibody, a BCL-2 inhibitor, a BTK inhibitor, a P13Kδ inhibitor, rituximab, a platinum-based drug, an antimetabolite, ibrutinib, idelalisib, fludararbine (fludarabine phosphate, FLUDARA®), anthracyclines, a BCR pathway inhibitor, ABT-199 (Venetoclax), or another chemotherapeutic agent used for treating a hematologic cancer. Other non-limiting examples of chemotherapeutic agents include alkylating agents, cytoskeletal disruptors, epothiolones, histone deacetylase inhibitors, inhibitors of topoisomerase I, inhibitors of topoisomerase II, nucleotide analogs and precursor analogs, antibiotics, platinum-based agents, retinoids, vinca alkaloids, or a combination thereof.

In some embodiments, the patient has resistance to an anti-CD20 antibody, a BCL-2 inhibitor, a BTK inhibitor, a P13Kδ inhibitor, a platinum-based drug, an antimetabolite, an anthracycline, a BCR pathway inhibitor, or another chemotherapeutic agent used for treating a hematologic cancer. In some embodiments, the patient has resistance to a drug selected from the group consisting of ABT-199 (venetoclax), rituximab, ibrutinib, idelalisib, and fludararbine (fludarabine phosphate, FLUDARA®). In some embodiments, the patient has resistance to ibrutinib.

In some embodiments, the patient was previously administered a drug for treating a hematological cancer. Non-limiting examples the drug include an alkylating agent, an anti-CD20 antibody, a BCL-2 inhibitor, a BTK inhibitor, a P13Kδ inhibitor, rituximab, a platinum-based drug, an antimetabolite, ibrutinib, idelalisib, fludarabine (fludarabine phosphate, FLUDARA®), anthracyclines, a BCR pathway inhibitor, ABT-199 (venetoclax), and other agents used for treating a hematologic cancer. Other non-limiting examples of chemotherapeutic agents include cytoskeletal disruptors, epothiolones, histone deacetylase inhibitors, inhibitors of topoisomerase I, inhibitors of topoisomerase II, nucleotide analogs and precursor analogs, antibiotics, platinum-based agents, retinoids, vinca alkaloids, or a combination thereof.

In some embodiments, the patient was previously administered a drug selected from the group consisting of an alkylating agent, an anti-CD20 antibody, a BCL-2 inhibitor, a BTK inhibitor, a P13Kδ inhibitor, a platinum-based drug, an antimetabolite, an anthracycline, a BCR pathway inhibitor, and another chemotherapeutic agent used for treating a hematologic cancer. In some embodiments, the patient was previously administered a drug selected from the group consisting of venetoclax, rituximab, ibrutinib, idelalisib, and fludararbine. In some embodiments, the drug is R-CHOP (Rituximab; Cyclophosphamide; Doxorubicin hydrochloride; Oncovin (vincristine); Prednisone). In some embodiments, the drug is R-CVP (Rituximab; Cyclophosphamide; Vincristine; Prednisone). In some embodiments, the drug is bevacizumab. In some embodiments, the drug is a combination of fludarahine and rituximab, a combination of bendamustine and rituximab, or a combination of bevacizumab and rituximab.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

In some embodiments, methods of treating a relapsed or refractory hematologic cancer in a human patient in need thereof comprises administering to the patient a daily dose of about 10 mg to about 75 mg of cerdulatinib or a pharmaceutically acceptable salt thereof or a pharmaceutical composition comprising a daily dose of about 10 mg to about 75 mg of cerdulatinib or a pharmaceutically acceptable salt thereof, and at least one pharmaceutically acceptable carrier or excipient.

In some embodiments, methods of treating a relapsed or refractory hematologic cancer in a human patient in need thereof comprise administering to the patient a twice daily a dose of about 45 mg of cerdulatinib or a pharmaceutically acceptable salt thereof.

In some embodiments, methods of treating a relapsed or refractory hematologic cancer in a human patient in need thereof comprise administering to the patient a twice daily a dose of about 35 mg of cerdulatinib or a pharmaceutically acceptable salt thereof.

In some embodiments provided herein, the daily dose of cerdulatinib is about 10 mg to about 75 mg. In some embodiments provided herein, the daily dose of cerdulatinib is about 25 mg to about 45 mg. In some embodiments, the daily dose of cerdulatinib is about 15 mg, 30 mg, 45 mg, or 50 mg.

In some embodiments, the daily dose of cerdulatinib is about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 95 mg, about 100 mg, about 105 mg, or about 110 mg. In some embodiments, the daily dose of cerdulatinib is about 90 mg. In some embodiments, the daily dose of cerdulatinib is about 70 mg. In some embodiments, the daily dose of cerdulatinib is administered twice daily at about 35 mg per dose.

In some embodiments, the administration of cerdulatinib is once daily. In some embodiments, the administration is twice daily. In some embodiments, the administration is three times daily.

In certain embodiments, the therapeutically effective amount of cerdulatinib used in the methods provided herein is at least about 10 mg per day. In one embodiment, the therapeutically effective amount of cerdulatinib is at least about 10, 20, 30, 40, or 50 mg per dosage. In one embodiment, the therapeutically effective amount of cerdulatinib is at least about 10, 20, 30, 40, 50, 60, 70, 80, 90 or 100 mg per day.

In one embodiment, the therapeutically effective amount of cerdulatinib is at least 30 mg, 35 mg, 40 mg, 45 mg, 50 mg, 55 mg, 60 mg, or 65 mg per day. In one embodiment, the therapeutically effective amount of cerdulatinib is at least about 15 mg, 20 mg, 25 mg, 30 mg, or 35 mg and is administered twice daily.

In certain embodiments, the therapeutically effective amount of cerdulatinib is no more than about 500, 400, 300, 200, 150, 120, or 100 mg per day. In one embodiment, the therapeutically effective amount of cerdulatinib is no more than about 300, 200, 150, 120, 100, 90, 80, 70, 60, 55 or 50 mg per dosage.

In certain embodiments, the therapeutically effective amount of cerdulatinib is no more than about 100 mg, 95 mg, 90 mg, 85 mg, 80 mg, or 75 mg per day. In certain embodiments, the therapeutically effective amount of cerdulatinib is no more than 45 mg, 40 mg, 35 mg, or 30 mg and is administered twice daily.

In one embodiment, the therapeutically effective amount of cerdulatinib, whether alone or in combination with another agent, is administered at from about 10 mg to 200 mg, from about 25 mg to 150 mg, from about 50 to 120 mg, from about 80 to 100 mg a day.

In one embodiment, the therapeutically effective amount of cerdulatinib, whether alone or in combination with another agent, is 25 mg to 120 mg daily. In some embodiments, the effective amount of cerdulatinib is 25 mg to 50 mg twice daily.

In one embodiment, the therapeutically effective amount cerdulatinib, whether alone or in combination with another agent, is administered at from about 10 mg to 150 mg, from about 25 mg to 120 mg, from about 30 to 80 mg, from about 40 to 50 mg a dosage, once or twice a day. In certain embodiments, the cerdulatinib, whether alone or in combination with another agent, is administered once, twice, three times, or four times a day.

In one embodiment, the cerdulatinib, whether alone or in combination with another agent, is administered from about 30 mg to about 80 mg once a day. In one embodiment, the cerdulatinib, whether alone or in combination with another agent, is administered from about 15 mg to about 40 mg twice a day.

In one embodiment, 45 mg of cerdulatinib, whether alone or in combination with another agent, is administered twice daily. In one embodiment, 35 mg of cerdulatinib, whether alone or in combination with another agent, is administered twice daily.

In some embodiments, the effective amount of cerdulatinib, or a pharmaceutically acceptable salt thereof, is about 40 mg to about 50 mg administered twice daily.

In some embodiments, the effective amount of cerdulatinib, or a pharmaceutically acceptable salt thereof, is about 30 mg to about 40 mg administered twice daily.

In another embodiment, the present disclosure provides a method of treating a cancer in a subject in need thereof by administering to the subject an effective amount of a composition comprising cerdulatinib in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, hone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, -ray, or electron, proton, neutron, or particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexatin lutetium), surgery, or bone marrow and stem cell transplantation.

3. Pharmaceutical Compositions and Kits

Some embodiments provided herein are directed to pharmaceutical compositions comprising an effective amount of cerdulatinib and at least one pharmaceutically acceptable carrier or excipient.

Carriers or excipients can be used to produce compositions. The carriers or excipients can be chosen to facilitate administration of the compound, such as cerdulatinib. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, PA, 2005 (hereby incorporated by reference herein).

Cerdulatinib can be administered by different routes including intravenous, intraperitoneal, subcutaneous, intramuscular, oral, transmucosal, rectal, transdermal, or inhalant. In some embodiments, cerdulatinib can be administered by oral administration. For oral administration, for example, cerdulatinib can be formulated into conventional oral dosage forms such as capsules, tablets, and liquid preparations such as syrups, elixirs, and concentrated drops.

For inhalants, cerdulatinib may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. Cerdulatinib may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining cerdulatinib with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, cerdulatinib may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, cerdulatinib is formulated in sterile liquid solutions, such as in physiologically compatible buffers or solutions, such as saline solution, Hank's solution, or Ringer's solution. In addition, cerdulatinib may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this disclosure are formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In another embodiment, the carriers are those in which the active ingredient is soluble. Emulsifiers, stabilizers, humectants and antioxidants may also be included as well as agents imparting color or fragrance, if desired. Creams for topical application are formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

In another embodiment, the present disclosure provides kits that include cerdulatinib or a pharmaceutically acceptable salt thereof or a pharmaceutical composition thereof. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the kits described herein may include written instructions for use and/or other indication that the compound or composition is suitable or approved for administration to a mammal, e.g., a human, for a disease or condition as described herein, such as a hematologic cancer; and the compound or composition may be packaged in unit dose or single dose form, e.g., single dose pills, capsules, or the like.

EXAMPLES

Example 1: Preclinical Models, Clinical PK/PD, and Tumor Response

Materials and Methods

Purified Kinase Assays: Performed at Millipore at a fixed concentration of 300 nM ATP. A 10-point concentration curve was used to determine IC (Inhibitory Concentration).

Human Whole Blood Assays: Inhibition of SYK- and JAK-dependent and independent signaling was determined by stimulating human whole blood with various agonists against BCR and cytokine receptors. 100 µL aliquots of heparinized healthy human whole blood was stimulated as previously described (Coffey et al, J. of Pharm. and Experimental Therapeutics, 351:538-548, 2014), using an 8-point concentration curve to determine $IC_{50}$'s. Signaling and activation responses were determined by Fluorescence-activated cell sorting ("FACS"). For the clinical trial, whole blood samples were collected prior to and after dosing. Percent inhibition was calculated by normalizing to the pre-dose stimulation response.

DLBCL Cell Line Viability Assays: Cell lines, purchased from ATCC, were screened using the CellTiter Glo (Promega) assay in 384 well plates using a ten-point concentration response curve to generate $IC_{50}$'s. Each $IC_{50}$ value is an average of at least four replicate experiments. Subsequent analysis using a FACS based caspase 3 cleavage detection kit (BD Biosciences) and Edu incorporation were performed.

Rat Collagen Induced Arthritis: In vivo anti-inflammatory activity of cerdulatinib was determined using the rat collagen induced arthritis model and performed exactly as described elsewhere (Coffey et al, J. of Pharm. and Experimental Therapeutics, 340: 350-359, 2012). Collagen antibody titers were determined by ELISA (R&D Systems). Steady-state serum Cmax was determined using liquid chromatography-tandem mass spectrometry.

Cytokine Analysis: Serum protein was analyzed by Myriad RBM (Austin, TX) using the Human Inflammation Map.

Clinical Study Design. This is a Phase 1 open-label, multi-dose, dose escalation study of cerdulatinib in patients with relapsed/refractory CLL/SLL or B-cell NHL. Study initiated at 15 mg QD (once daily) and dose-escalated in a 3+3 design with a 28 day safety window. Patients received a single dose on day 1 for 72 hour PK evaluation. Continuous dosing was then initiated on day 4.

Results

In healthy whole blood ex vivo spiking experiments, cerdulatinib selectively inhibited BCR/SYK and cytokine (IL2, IL4, IL6) JAK/STAT signaling with $IC_{50}$'s ranging from 0.2-0.9 µM (achieved at clinical doses of 15 mg to 40 mg), arrested inflammation and joint destruction in the rat collagen-induced arthritis model at 0.3 µM average plasma concentration (achieved at doses≥30 mg), and induced apoptosis in the majority of cell lines at 2 µM (achieved at doses≥40 mg). Plasma concentrations above 2 µM have been safely achieved in cancer patients following once daily oral dosing, while maintaining steady-state Cmin of ~1 µM.

Cerdulatinib Potency and Specificity Against SYK and JAK Signaling

Table 1 represents cerdulatinib $IC_{50}$'s against purified kinases that were inhibited >80% in a 270 kinase panel screen (Millipore). Despite inhibition in enzyme reactions, there is no evidence of inhibition at the cellular level and/or in patients for AMPK, JAK2, TBK-1, RSK2, and RSK4.

TABLE 1

| Purified Kinase Assays | |
| --- | --- |
| KINASE | $IC_{50}$ (nM) |
| TYK2 | 0.5 |
| MST1 | 4 |
| ARK5 | 4 |
| MLK1 | 5 |
| FMS | 5 |
| AMPK | 6 |
| JAK2 | 6 |
| JAK3 | 8 |
| TBK1 | 10 |
| MARK1 | 10 |
| JAK1 | 12 |
| PAR1B-a | 13 |
| TSSK | 14 |
| MST2 | 15 |
| GCK | 18 |
| JNK3 | 18 |
| RSK2 | 20 |
| RSK4 | 28 |
| SYK | 32 |
| CHK1 | 42 |
| FLT4 | 51 |
| FLT3 | 90 |
| RET | 105 |
| ITK | 194 |

Table 2 is a summary of cerdulatinib IC's in various healthy normal human whole blood assays. This data demonstrates selectivity for SYK, JAK1/3, and JAK1/TYK2 dependent pathways. Potency against SYK and JAK1/3/TYK2 pathways are comparable.

TABLE 2

| Healthy Normal Human Whole Blood Assays | | | | |
| --- | --- | --- | --- | --- |
| CELL TYPE | STIMULATION | KINASE | READOUT | $IC_{50}$ (µM) |
| B-cell | BCR | SYK | CD69 | 0.1 |
| | BCR | SYK | pERK Y204 | 0.5 |
| | IL4 | JAK1/3 | pSTAT6 Y641 | 0.92 |
| | PMA | PKC | pERK Y204 | >4 |
| Basophil | FcεR1 | SYK | CD63 | 0.12 |
| T-cell | IL2 | JAK1/3 | pSTAT5 Y694 | 0.2 |
| | IL4 | JAK1/3 | PSTAT6 Y641 | 0.58 |
| | TCR | Zap70 | pERK Y204 | >4 |
| | PMA | PKC | pERK Y204 | >4 |
| Monocytes | IL6 | JAK1/TYK2 | pSTAT3 Y705 | 0.35 |
| | GMCSF | JAK2 | pSTAT5 Y694 | >4 |

Cerdulatinib is Broadly Active Against 15 DLBCL Cell Lines at 2 µM.

Cerdulatinib demonstrated broad anti-tumor activity in DLBCL cell lines, relative to more targeted agents. Table 3 below summarizes $IC_{50}$ values of cerdulatinib compared to other relevant kinase inhibitors: PRT06318 (Syk inhibitor, which is described in U.S. Pat. No. 6,432,963); InSolution™ JAK Inhibitor I (CAS 457081-03-7; "Pan-Jak" in Table 3); CP-690550 (Jak3 Inhibitor); Idelalisib (PI3Kδ inhibitor); IPI-145 (PI3Kδ and γ inhibitor); and Doxorubicin ("Doxo;" anthracycline). These inhibitors are commercially available or are made according to synthetic methods known to those skilled in the art.

TABLE 3

| $IC_{50}$ of Kinase Inhibitor in CellTiter Glo Assay | | | | | | | |
| --- | --- | --- | --- | --- | --- | --- | --- |
| Cell Line | Cerdulatinib | PRT06-318 | Pan-Jak | CP690550 | Idelalisib | IPI-145 | Doxo |
| LY18 | 1.0 | 2.8 | 0.8 | 50 | 3.8 | 0.96 | 0.06 |
| VAL | 2.7 | 4.5 | 5.2 | 50 | 29 | 21 | 0.22 |
| DHL6 | 1.2 | 0.9 | 2.63 | 50 | 0.03 | 0.002 | 0.14 |
| LY10 | 0.29 | 0.31 | 5.1 | 50 | 12 | 5.7 | 0.04 |
| DHL4 | 1.4 | 1.1 | 50 | 28 | 12 | 3.7 | 0.10 |
| DHL5 | 0.31 | 0.44 | 39 | 41 | 1.3 | 0.33 | 0.03 |
| U2932 | 2.6 | 8 | 3.9 | 50 | 40 | 27 | 0.35 |
| LY1 | 4.4 | 10 | 0.7 | 50 | 4.9 | 1.3 | 0.19 |
| DHL10 | 2.3 | 20 | 40 | 50 | 12 | 4.1 | 0.30 |

TABLE 3-continued

| | IC$_{50}$ of Kinase Inhibitor in CellTiter Glo Assay | | | | | | |
|---|---|---|---|---|---|---|---|
| Cell Line | Cerdulatinib | PRT06-318 | Pan-Jak | CP690550 | Idelalisib | IPI-145 | Doxo |
| LY7 | 1.9 | 9 | 34 | 50 | 13 | 25 | 0.14 |
| DHL8 | 3.1 | 19 | 28 | 38 | 49 | 45 | 0.15 |
| DLCL2 | 5.4 | 9 | 42 | 50 | 15 | 5 | 0.18 |
| DB | 14 | 30 | 21.4 | 50 | 42 | 50 | 0.37 |
| TOLEDO | 6.9 | 15 | 5.9 | 41 | 50 | 18 | 0.44 |
| RCK8 | 15.6 | 22 | 43 | 50 | 50 | 50 | 0.20 |

In a panel of 15 cell lines representing both ABC and GCB subtypes, 9 underwent apoptosis and an additional 2 underwent cell cycle arrest. Cooperative effects of SYK and JAK inhibition were observed in 4 of the cell lines, whereas 3 cell lines were sensitive to SYK but not JAK inhibition, and 1 cell line was sensitive to JAK but not SYK inhibition. Three of the 15 cell lines (DB, TOLEDO, and RCK8) were resistant to cerdulatinib.

Figure 2:
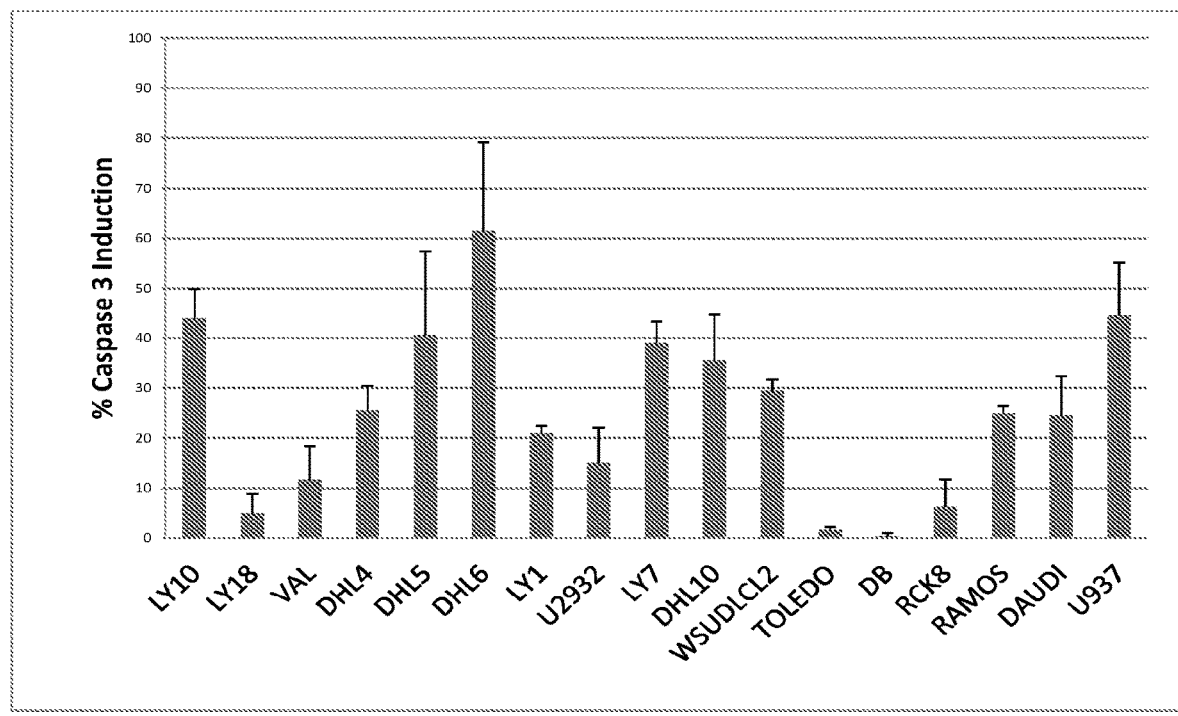
FIG. 2 provides a bar graph that depicts inhibition of precedent induction of caspase 3 cleavage by FACS analysis in a variety of DLBCL cell lines at 2 μM of cerdulatinib at 72 hours.

FIG. 1 and FIG. 2 depicts bar graphs that show the percent inhibition of Edu incorporation and percent induction of caspase 3 cleavage by FACS analysis, respectively.

The above data demonstrates that cerdulatinib is broadly active against DLBCL cell lines at 2 µM and acts predominately by inducing apoptosis.

Cerdulatinib Arrests Autoimmune Mechanisms at 0.52 µM $C_{max}$ in Rats.

Figure 3:
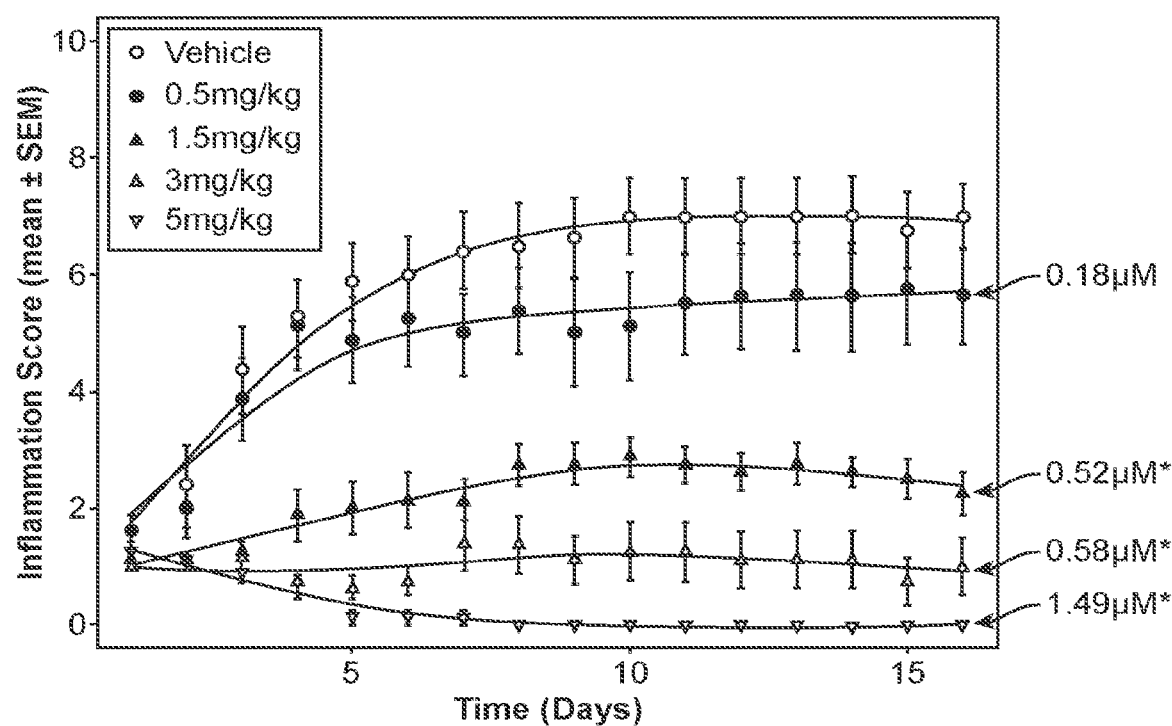
FIG. 3 provides hind paw inflammation scores (mean±standard error of mean ("SEM"); y-axis; n=8 per group) are plotted over time (x-axis) while treated with vehicle or various dose levels of cerdulatinib. The average plasma concentrations ($C_{max}$) for each dosing group is shown at the right of the graph. Asterisks denote statistical significant relative to vehicle by student T test (p<0.05).

FIG. 3 shows data from a rat collagen induced arthritis model. Hind paw inflammation scores (mean±SEM; y-axis; n=8 per group) are plotted over time (x-axis) while treated with vehicle or various dose levels of cerdulatinib. The average plasma concentrations ($C_{max}$) for each dosing group is shown at the right of the graph. Asterisks denote statistical significant relative to vehicle by student T test (p<0.05).

Inflammation and auto-antibody generation in rats were completely arrested at cerdulatinib plasma concentrations of between 0.5-0.6 µM $C_{max}$ (corresponding to ~0.3-0.4 µM $C_{average}$). These exposures are safely achieved in humans at the 30 mg once daily dose, and correspond to approximately 50% inhibition of SYK and JAK in peripheral whole blood assays. Clear evidence for reduction of serum β2M (and other inflammation markers) was observed at all dose levels tested clinically.

Potency of SYK and JAK Inhibition Following Oral Dosing in Patients.

Following oral dosing in patients, SYK and JAK pathways were inhibited with similar potency as was observed in healthy volunteer ex vivo spiking experiments, and >90% inhibition of SYK and JAK has been safely achieved for multiple cycles of therapy.

Tumor response as measured by CT scan significantly correlated with percent inhibition of SYK and JAK signaling in patient-derived whole blood, and percent inhibition of serum markers of inflammation (e.g. β2M, CRP, IL10, VCAM1, sTNFR, CCL3).

Conclusions

Cerdulatinib concentrations required to induce apoptosis and/or cell cycle arrest are variable but generally observed at 2 µM. Steady-state concentrations of 1-2 µM $C_{min}$ to $C_{max}$ are safely achieved at 40 mg QD. Patient tumor reductions as assessed by CT scan significantly correlate with % inhibition of SYK and JAK, % inhibition of several serum inflammation markers and is also related to cerdulatinib plasma concentration. Dose escalation continues with good tolerability up to 100 mg QD.

Based on these results, it is contemplated that cerdulatinib is useful for treatment of B-cell lymphomas, such as DLBCL.

Example 2: Effect of the Cerdulatinib on Primary Human CLL Cells

Cerdulatinib in 24 Primary CLL Samples

CLL cell isolation and culture: CLL cells (commercially available from ATCC) were purified using the Human B cell Enrichment Cocktail Kit (Stemcell Technologies, Vancouver, BC, Canada) and were stained with anti-CD5/CD19 for verification of the purity, which was greater than 95% for all cases. Isolated CLL cells were cultured in RPMI-1640 with 15% fetal bovine serum (Gibco, Grand Island, NY, USA), penicillin (100 IU), and streptomycin (100 µg/mL), at a density of $1\times10^7$ cells/mL in the presence or absence of 2.5 mg/mL CpG, 100 ng/mL CD40L, 10 ng/mL IL-4. Anti-IgM stimulation was conducted with plate-bound anti-IgM (10 µg/mL). CLL cells were stimulated with 10 ng/mL IL-6 (R&D Systems, Minneapolis, MN), to detect the phosphorylation of JAK1/JAK2 (Cell Signaling Technology, Danvers, MA) and STAT3 (Cell Signaling Technology, Danvers, MA, USA).

Cell viability assay and IC$_{50}$ determination: Isolated CD5$^+$/CD19$^+$ cells from CLL patients were incubated with or without increasing concentrations of cerdulatinib ($10^1$-$10^5$ nM) for 72 hours and cell viability was measured by staining with 2 µg/mL propidium iodide (PI) (Molecular Probe), as previously described. Ten thousand events in a live cell gate were counted by a FACS LSR2 (BD Biosciences) and the data was normalized to the matched vehicle control for each specimen (100%). IC$_{50}$ was then generated using the GraphPad Prism 6 program (San Diego, CA, USA).

Co-culture conditions: Human bone marrow stromal cell line HS-5 was obtained from ATCC and NK-Tert (NKTert) was kindly provided by Dr. Jan A. Burger (M. D. Anderson), CLL cell and stromal cell co-culture assays were described previously (e.g. Cheng et al., *Leukemia*. 2014; 28(3):649-657). Briefly, stromal cells were seeded at a concentration of $5\times10^4$ cells/per well in 24-well plates and were incubated for 24 hours to allow cells to adhere. CLL cells were then added to the culture at a ratio of 100:1 ($5\times10^6$ cells/mL) on confluent layers of stromal cells in RPMI medium. CLL cells were harvested by gentle pipetting, leaving the adherent stromal cell layer intact.

Primary CLL samples with serial diluted cerdulatinib and measured cell viability after 72 hours with PI/7AAD flow cytometry.

Twenty four primary CLL samples were treated with cerdulatinib, a dual SYK/JAK inhibitor in the presence or absence of IL-4/CD40L and apoptosis assessed using propidium iodide/Annexin V staining and PARP cleavage. The effect of cerdulatinib on B cell receptor and cytokine receptor induced signalling was assessed by immunoblotting and flow cytometry.

CLL cells from 24 patients were treated with cerdulatinib for 24, 48 and 72 hours and viability assessed using propidium iodide and Annexin V staining. Cerdulatinib induced apoptosis in a concentration and time dependent manner.

Unmutated IGHV and high expression of CD49d are associated with progressive disease and a worse prognosis in CLL. Importantly for therapeutic use, cerdulatinib induced significantly greater apoptosis in U-CLL compared to M-CLL and in CLL cells with high CD49d or ZAP70 expression (>30%) compared to CLL cells with low CD49d or ZAP70 expression (<30%).

Treatment of CLL cells with cerdulatinib was found to induce cleavage/activation of the pro-apoptotic caspase 3 protein and also increased levels of the 85 kDa PARP sub-fragment, a marker of apoptosis. Cerdulatinib induced apoptosis was inhibited by co-treatment with the caspase inhibitor ZVAD, indicating that cerdulatinib induced apoptosis of CLL cells occurs via a caspase dependent mechanism. In addition, levels of the pro-apoptotic protein NOXA were increased after 24 hours of cerdulatinib treatment in the presence of ZVAD, whilst the anti-apoptotic protein MCL1 was decreased.

Ligation of the BCR in lymph nodes enhances CLL survival and resistance to chemotherapy. Cerdulatinib pretreatment was able to inhibit both soluble anti-IgM and immobilised anti-IgM induced signalling pathways. IL-4 signals via the JAK/STAT-6 pathway in CLL cells and has been shown to be important in mediating protection from chemotherapy. Treatment of CLL cells with cerdulatinib abrogated IL-4 induced STAT6 phosphorylation. In addition, cerdulatinib inhibited TL-4 increased surface IgM expression after 24 hours in the presence of ZVAD.

In patients, lymph node tissue sites provide various signals which protect CLL cells from apoptosis. We have therefore used IL-4 and CD40L to mimic the lymph node environment in vitro. IL-4/CD40L treatment after 24 hours increased the viability of CLL cells compared to non-treated cells.

This Example shows that treatment of primary human CLL cells with cerdulatinib induced caspase dependent apoptosis, with increased potency in CLL samples poor prognostic markers; cerdulatinib overcame BCR and IL-4 mediated signalling at concentrations achievable in patients (~2.2 µM); and cerdulatinib induced apoptosis in the presence or absence of IL-4/CD40L support.

Cerdulatinib in 60 CLL Samples

In 60 CLL samples analyzed according to the methods described above, $IC_{50}$ in 60 CLL ranged from 0.37 to 10.02 µM. The average $IC_{50}$ of cerdulatinib for the cohort was 2.57 µM, which is clinically achievable.

Figure 6:
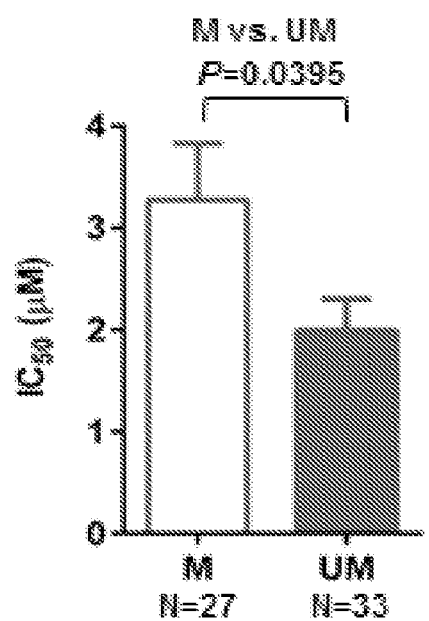
FIG. 6 shows that CLL cells with unmutated ("UM") IGHV (N=33) are more sensitive to cerdulatinib than IGHV mutated ("M") CLL (N=27). Data was analyzed with Student T test. mean+SE of $IC_{50}$ are plotted. P=0.0395.
Figure 7:
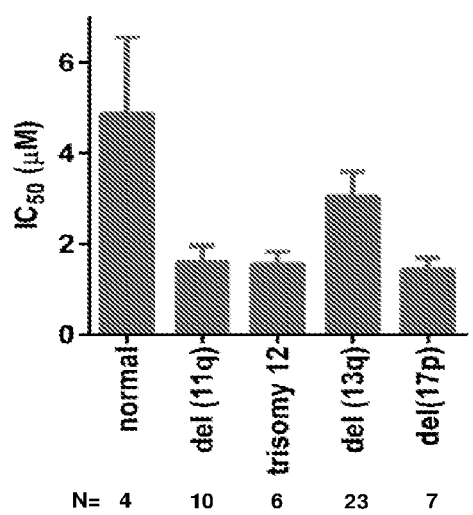
FIG. 7 shows cerdulatinib sensitivity of CLL cells with different cytogenetic abnormalities. Case numbers for each subgroup are indicated. Data was analyzed by ANOVA test, mean+SE of $IC_{50}$ are plotted.*, P<0.05.

Whether cell killing by cerdulatinib differs among CLL subgroups stratified by known prognostic factors was also studied. It was found that CLL cells with unmutated IGHV (N=33) versus mutated IGHV (N=27) have lower $IC_{50}$s and thus were more sensitive to cerdulatinib (P=0.0395) (data analyzed with Student Test) (FIG. 6). CLL cells with high-risk genetic abnormalities (including del (11q), trisomy 12, and del(17p)) were also more sensitive to cerdulatinib than those with del (13q) or lacking these specific genetic anomalies altogether (FIG. 7). Thus, CLL cells are sensitive to cerdulatinib, especially in cases with poor prognosis by IGHV and cytogenetics.

It is also contemplated that cerdulatinib will also be useful in cases of poor prognosis as evidenced by, for example, Zap70.

Example 3: Clinical and Correlative Results of a Phase I Study of Cerdulatinib

A first-in-human study of cerdulatinib in patients with relapsed/refractory CLL/SLL or B-cell non-Hodgkin's lymphoma (NHL) was carried out. A 3+3 dose escalation study with 28-day cycles was carried out; the doses studied ranged from 15 mg to 65 mg once daily and up to 45 mg twice daily. Patients received a single dose on day 1 for 72 hour PK evaluation. Continuous dosing was initiated on day 4. 43 patients with CLL/SLL or B cell NHL were dosed. Median age was 67 years (range 23-85) and median prior therapies (tx) was 3 (range 1-8).

Pharmacokinetics ("PK"), pharmacodynamics ("PD"), and safety were monitored. Response was assessed by standard criteria. The level of inhibition of SYK and JAK was determined using a variety of whole blood assays measuring signaling via receptors for the B-cell antigen, IL2, IL4, IL6, and GM-CSF. Serum markers of tumor burden, including CCL3, CCL4, and other markers of inflammation (β2M and CRP), were also being measured.

It was observed that PK was suitable for once daily dosing with a half-life of 12-16 hours and a 2:1 peak-trough ratio. At day 28 of cycle 1, saturating inhibition of SYK and JAK in circulating lymphocytes (80-90% inhibition) and serum inflammation markers (e.g., β2M, CRP, CCL4; 50-90% inhibition) occurred at plasma concentrations of about 0.6 to 1 µM, achieved at $C_{min}$ of the 40 mg dose. At the 65 mg dose, these parameters were 80-90% inhibited on day 1 of cycle 1 indicating a more immediate effect compared to lower doses. At the 65 mg dose, steady state $C_{min}$ and $C_{max}$ concentrations were approximately 1 and 2 µM, respectively, sufficient to induce apoptosis in the majority of B cell lymphoma cell lines tested.

In general, cerdulatinib has been well tolerated. Ten total patients have remained on cerdulatinib for over 200 days, including 2 who have been on for a year or more.

Table 4 summarizes data of the steady state pharmacokinetics following oral dosing where n=28.

TABLE 4

| | Steady State PK Following Oral Dosing | | | | |
|---|---|---|---|---|---|
| Dose Group | SS Cmin µM | SS Cmax µM | SS Cave µM | AUC_tau µM * hr | $T_{1/2}$ hr |
| 15 mg/day | 0.12 ± 0.04 | 0.38 ± 0.04 | 0.19 ± 0.03 | 4.5 ± 0.8 | 11.5 ± 3.9 |
| 30 mg/day | 0.21 ± 0.12 | 0.63 ± 0.18 | 0.31 ± 0.12 | 7.5 ± 3.0 | 12.3 ± 6.8 |
| 40 mg/day | 0.87 ± 0.07 | 1.48 ± 0.15 | 1.14 ± 0.03 | 27.3 ± 0.8 | 32.8 ± 17.0 |

TABLE 4-continued

Steady State PK Following Oral Dosing

| Dose Group | SS Cmin μM | SS Cmax μM | SS Cave μM | AUC_tau μM * hr | $T_{1/2}$ hr |
|---|---|---|---|---|---|
| 45 mg/day* | 0.82 ± 0.6 | 1.69 ± 0.6 | 1.11 ± 0.6 | 26.6 ± 13.9 | 22.3 ± 15.5 |
| 50 mg/day | 0.90 ± 0.14 | 2.07 ± 0.54 | 1.31 ± 0.41 | 31.36 ± 9.95 | NA |
| Twice daily ("BID") Regimens | | | | | |
| 15 mg/twice daily | 0.29 ± 0.11 | 0.53 ± 0.13 | 0.39 ± 0.11 | 4.7 ± 1.3 | 11.2 ± 4.3 |
| 20 mg/twice daily | 0.38 ± 0.02 | 0.89 ± 0.16 | 0.52 ± 0.09 | 6.2 ± 1 | 8.4 ± 1.8 |

*PK outlier (steady state Cmax of 0.15 μM) was removed from the group.

Where n=20, at a dose group of 45 mg BID, the following was observed: $C_{min}$=1.27±0.6 μM; $C_{max}$=2.16±0.5 μM; $C_{ave}$=1.4±0.7 μM; AUC_tau=33.3±15.9 μM*hr; $T_{1/2}$=27.5±22.5 hr.

It was observed that complete inhibition of BCR signaling was observed in whole blood from a FL patient following a single 65 mg dose of cerdulatinib.

Table 5 summarizes the PK/PD data where n=43.

TABLE 5

PK/PD of Dose Groups

| Dose Group | SS Cmin μM | SS Cmax μM | SS Cave μM | AUC_tau μM * hr | $T_{1/2}$ hr | % Inh. BCR ($C_{min}$-$C_{max}$) Extrapolated from PK/PD fit of all data | % Inh. IL4 ($C_{min}$-$C_{max}$) |
|---|---|---|---|---|---|---|---|
| 15 mg/day | 0.12 ± 0.04 | 0.38 ± 0.04 | 0.19 ± 0.03 | 4.5 ± 0.8 | 11.5 ± 3.9 | 22-55% | 16-42% |
| 30 mg/day | 0.21 ± 0.12 | 0.63 ± 0.18 | 0.31 ± 0.12 | 7.5 ± 3.0 | 12.3 ± 6.8 | 31-83% | 26-57% |
| 40 mg/day | 0.87 ± 0.07 | 1.48 ± 0.15 | 1.14 ± 0.03 | 27.3 ± 0.8 | 32.8 ± 17.0 | 92-100% | 63-78% |
| 45 mg/day | 0.82 ± 0.6 | 1.69 ± 0.6 | 1.11 ± 0.6 | 26.6 ± 13.9 | 22.3 ± 15.5 | | |
| 50 mg/day | 0.79 ± 0.37 | 1.57 ± 0.94 | 0.99 ± 0.62 | 23.8 ± 14.9 | 39.0 ± 12.4 | | |
| 65 mg/day | 0.76 ± 0.04 | 1.67 ± 0.09 | 1.01 ± 0.03 | 24.2 ± 0.7 | 25.1 ± 6.5 | | |
| 100 mg/day (one patient) | 0.37 | 1.11 | 0.68 | 16.3 | 14.4 | 53-98% | 41-72% |
| 15 mg/twice daily | 0.29 ± 0.11 | 0.53 ± 0.13 | 0.39 ± 0.11 | 4.7 ± 1.3 | 11.2 ± 4.3 | 42-74% | 34-51% |
| 20 mg/twice daily | 0.38 ± 0.02 | 0.89 ± 0.16 | 0.52 ± 0.09 | 6.2 ± 1 | 8.4 ± 1.8 | 55-95% | 42-66% |
| 45 mg/twice daily | 1.48 ± 0.33 | 1.8 ± 0.7 | 1.5 ± 0.45 | | | 100-100% | 95-95% |

In review of the 40-100 mg QD doses, the average steady state (SS) $C_{min}$ and $C_{max}$ concentrations plateaued at 0.77±0.41 and 1.63±0.56 μM, respectively, and the average steady state (SS) $C_{ave}$ concentration was found to be 1.07±0.44 μM, % Inhibition of BCR ($C_{min}$-$C_{max}$) was 92-100%, and the % Inhibition of IL4 ($C_{min}$-$C_{max}$) was 63-78%. QD dosing of 40-100 mg resulted in 50 to 100% (steady-state $C_{min}$ to $C_{max}$) inhibition of SYK and JAK signaling in peripheral blood, and significant inhibition of serum markers of inflammation.

Based on these results, it is contemplated that a daily dose of 10 mg to about 75 mg of cerdulatinib is useful for the treatment of hematological cancers in patients in need thereof.

The extent of inhibition of SYK and JAK signaling as well as inhibition of serum markers of inflammation significantly correlated with tumor response. While the PK is suitable for QD dosing with a $t_{1/2}$ of 12-16 hours and a 2:1 peak-trough ratio, it is contemplated that the pH-dependent low solubility limited dissolution, and physiologic modeling suggested that BID dosing would increase overall exposure.

This was accomplished with the 45 mg BID dose, where complete inhibition of SYK and JAK at SS $C_{min}$ in peripheral blood assays was observed, consistent with an approximate doubling in exposure. At the 45 mg BID dose, SS $C_{min}$ was increased to about 1.5 μM, a concentration sufficient to induce apoptosis in pre-clinical tumor models using both primary cells and cell lines. Subsequent evaluation of 45 mg BID doses in patients demonstrated higher $C_{min}$, $C_{max}$, and AUC values for all patients treated at this dose level and PD markers indicated complete inhibition of both pathways.

Treatment emergent adverse events ("AEs") of ≥grade 3 deemed related to study and occurring in 2 or more patients were: fatigue (n=5), anemia and neutropenia (n=3 each), and abdominal pain, neutrophil count decrease, and pneumonia (n=2 each). The highest overall exposure was achieved at the 45 mg BID dose, in which 2 dose limiting toxcities ("DLTs") occurred: grade 3 pancreatitis and grade 3 fatigue.

Based on the PK/AE profile, there appeared to be higher grades of adverse events at SS $C_{min}$ of 1.25-1.5 µM or greater. PK modeling indicated a dose of 35 mg BID would yield a SS $C_{min}$ of 1.02 µM, SS $C_{max}$ of 1.3 µM, SS $C_{ave}$ of 1.2 µM, 100-100% of % Inhibition of BCR ($C_{min}$-$C_{max}$), and 90-95% of % Inhibition of IL4 ($C_{min}$-$C_{max}$), which is predicted to be tolerable, efficacious, and provide consistent anti-tumor activity.

Consistent tumor responses were observed in relapsed/refractory CLL and FL patients with SS Cmin of 0.7 µM.

Partial responses were observed in 5 heavily pretreated patients with CLL, FL, and transformed DLBCL at doses ranging from 30-65 mg QD. Two partial responses were observed in the 45 mg BID dose group, one in a patient with FL and another with CLL. Responses typically occurred after 2 cycles of treatment. Multiple patients have demonstrated nodal reductions and maintained clinical benefit for over a year.

Conclusions

Cerdulatinib has been well-tolerated in subjects with lymphoid malignancies. Cerdulatinib demonstrated a favorable PK profile and good tolerability at high levels of SYK and JAK inhibition. PK data supported once daily dosing, maintaining substantial inhibition at $C_{min}$. Dose-dependent and selective inhibition of SYK/JAK signaling with maximal inhibition was greater than 80 percent; no inhibition of JAK2 or PKC detected. BCR signaling pathway was 90-100% inhibited at steady state $C_{min}$/$C_{max}$, JAK/STAT signaling is inhibited 60-80% $C_{min}$/$C_{max}$. PK data indicated a plateau of exposure from 40 mg to 100 mg oral once daily, resulting in sub-micromolar exposure (about 0.7 µM) at stead-state $C_{min}$. It is contemplated that solubility may be the reason. BID dosing overcomes this plateau in exposure and has enhanced PD effects.

Cerdulatinib significantly reduced multiple serum proteins in blood that are markers of inflammation, such as β2M, CRP, TNFR, and CCL3/4. Significant correlations were observed between tumor response and inhibition of serum markers of inflammation (e.g. β2M and CCL4).

Cerdulatinib has promising activity in heavily pre-treated patients. These data demonstrated evidence of clinical activity in this study of patients with relapsed/refractory B-cell malignancies. To date, partial responses have been observed, including in patients with CLL, FL, and DLBCL. Tumor reductions were seen in multiple patients, including those whose disease progressed on (or who could not tolerate) other BCR pathway inhibitors. Evidence of lymphocytosis was observed as seen with other BCR pathway inhibitors. Results also showed that cerdulatinib was well tolerated in these heavily pre-treated patients.

These results, including partial responses, provide additional evidence that cerdulatinib is active and well tolerated in patients with relapsed or refractory hematologic cancers.

Example 4: Cerdulatinib was Found to Block Proliferation of Ibrutinib-Sensitive and Ibrutinib-Resistant Primary CLL Cells and BTK$^{C481S}$ Transfected Cell Lines Ibrutinib was purchased from Selleckchem (Houston, TX, USA).

Cell isolation and culture: CLL cells were purified using the Human B cell Enrichment Cocktail Kit (Stemcell Technologies, Vancouver, BC, Canada) and were stained with anti-CD5/CD19 (clone HIB19 and UCHT2, respectively, eBioscience, San Diego, CA) for verification of the purity, which was greater than 95% for all cases. Isolated CLL cells were cultured in RPMI-1640 with 15% fetal bovine serum (Gibco, Grand Island, NY), penicillin (100 IU), and streptomycin (100 µg/mL), at a density of 1×10$^7$ cells/mL in the presence or absence of 2.5 mg/mL CpG (ODN2006, stimulatory CpG-ODN type B, human specific, purchased from Invivogen (San Diego, CA)), 100 ng/mL CD40L (Enzo Life Sciences, Plymouth Meeting, PA), 10 ng/mL IL-4 CD40L (Enzo Life Sciences, Plymouth Meeting, PA). Anti-IgM stimulation was conducted with plate-bound anti-IgM (10 µg/mL).

Cell proliferation assays: Bromodeoxyuridine (BrdU) was added at the 8-day culture with combined stimulation (2.5 µg/mL CpG, 100 ng/mL CD40L, 10 ng/mL IL-4 and 10 µg/mL plate-bound anti-IgM). The percentage of BrdU$^+$ cells was analyzed by flow cytometry using the BrdU Flow kit (BD Biosciences) according to the manufacturer's instructions.

Generation of BTK C481S and T316A mutant constructs: BTK wild type (WT) cDNA clone in pCMV6 expression vector was purchased from ORIGENE (Rockville, MD USA). BTK$^{C481S}$ and BTK$^{T316A}$ mutant vectors were generated using the QuikChange II Site-Directed Mutagenesis Kit (Agilent Technologies, Cedar Creek, TX, USA) following manufacturer's instructions. The identity of the mutant constructs was confirmed by Sanger sequencing.

Cell transfection, cell count and viability assay: TMD8 cells were transfected with constructs of WT BTK or BTK$^{C481S}$ mutants using kit V, Program U-13 on Amaxa Nucleofector, according to the manufacturer's protocols (Amaxa, Cologne, Germany). After transfection, the cells were co-cultured with NKTert cells in a 24-well plate for 24 hrs for recovery. Ibrutinib, cerdulatinib and vehicle (DMSO) were then added into the transfected TMD8 cells and cellular viability was determined with Muse™ Count & Viability kit using Muse Cell Analyzer (Millipore, Hayward, CA, USA).

Flow cytometry: Cell staining for FACS analysis was done with an optimized amount of fluorochrome conjugated mAbs as described previously (e.g. Cheng et al., *Leukemia*. 2014; 28(3):649-657). Briefly, after washing twice with washing buffer (1×PBS, 0.5% BSA, 0.1% NaN$_3$), 1×10$^6$ cells were suspended in 100 µL washing buffer and stained with fluorochrome conjugated mAbs and incubated for 20 min at room temperature. Cells were washed twice in Perm/Wash buffer before scanning by flow cytometer. For intracellular phosphoflow analysis, freshly isolated CLL cells were immediately fixed with 2-4% paraformaldehyde and stored at −80° C. The cryopreserved cells were thawed at room temperature and permeated with 50% methanol on ice for 4 h. 1×10$^6$ cells were suspended in 100 µL washing buffer and stained with fluorochrome conjugated mAbs and incubated for 20 min at room temperature. Flow cytometry was then conducted with LSR2 flow cytometer (BD Biosciences), and the data were analyzed using the FlowJo software (FLOWJO LLC, Ashland, OR, USA).

Primary cells isolated prior to ibrutinib therapy from patients who responded to ibrutinib were treated with either 250 nM of ibrutinib or cerdulatinib under the condition of combined stimulation. BrdU incorporation was measured at day 8. These cells responded equally well to either drug at this concentration.

Similar experiments on cells isolated from three ibrutinib-relapsed patients were also performed. These samples carry BTK mutations that confer ibrutinib resistance. Two of the patients had the known mutation $BTK^{C481S}$, and one other patient had $BTKT^{316A}$. Live cell number was counted daily for 7 days.

When these mutated cells were tested against ibrutinib and cerdulatinib, a significant number of BrdU$^+$ CLL cells remained following ibrutinib treatment, whereas cerdulatinib almost completely blocked the appearance of BrdU$^+$ cell populations in all three cases. These experiments demonstrate that cerdulatinib not only blocks cell proliferation in ibrutinib-sensitive but also ibrutinib-resistant CLL cells.

To test whether cerdulatinib directly suppresses the growth of ibrutinib-resistant cells, both $BTK^{C481S}$ and wild type BTK (WT) expression vectors were constructed, cloned, and then transfected into the ibrutinib-sensitive lymphoma cell line TMD8. Cell growth following exposure to ibrutinib or cerdulatinib was assessed.

Figure 4:
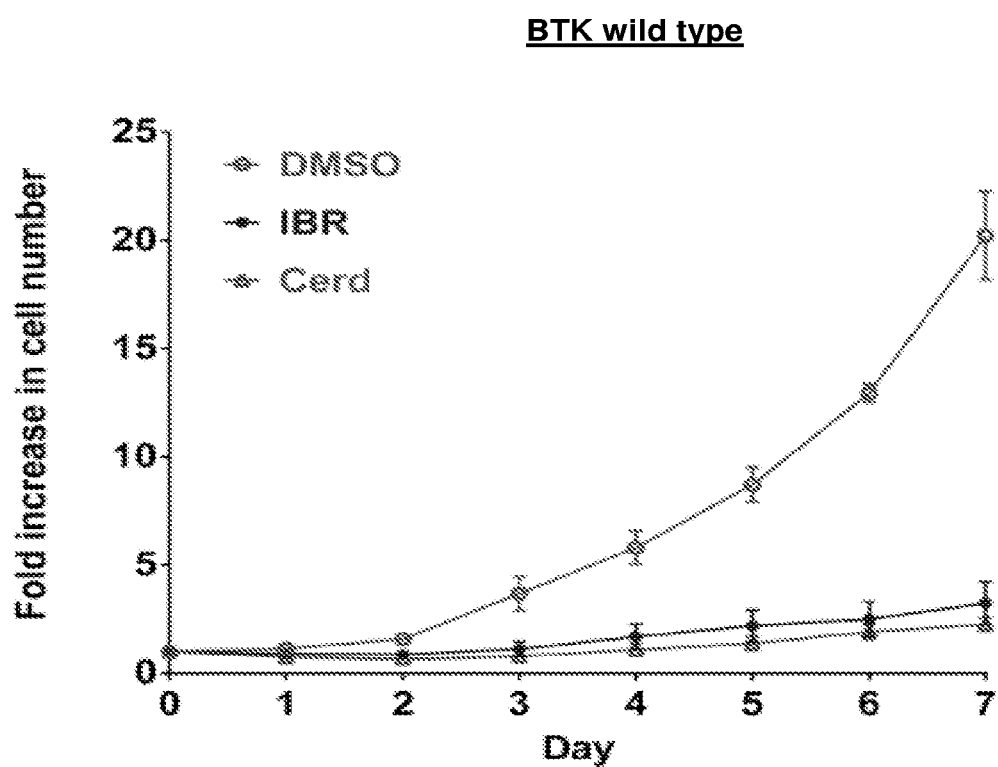
FIG. 4 shows the results of the effects of ibrutinib and cerdulatinib in WT BTK-transfected TMD8 cells. 250 nM of ibrutinib or cerdulatinib was added into the culture and live cell number was counted daily for 7 days. The results shown are the mean±standard error ("SE") of 4 replicate experiments. Open circle=dimethylsulfoxide ("DMSO"); closed circle=ibrutinib ("IBR"); triangle=cerdulatinib ("Cerd").
Figure 5:
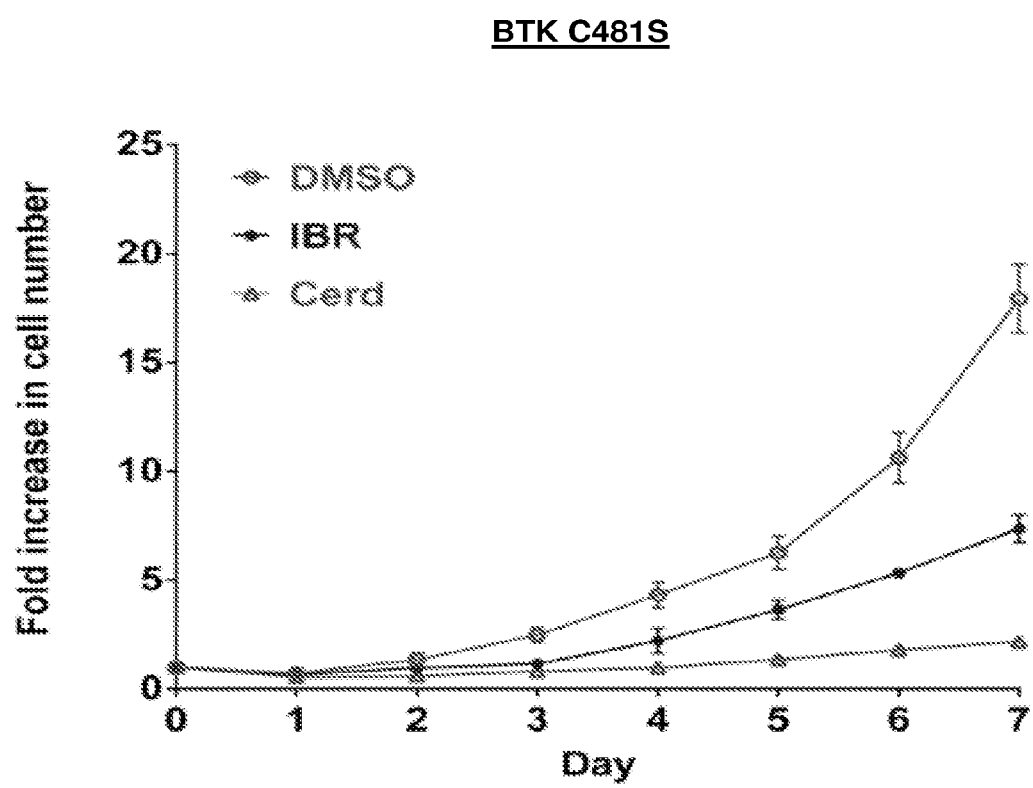
FIG. 5 shows the effects of ibrutinib and cerdulatinib in $BTK^{C481S}$-transfected TMD8 cells. 250 nM of ibrutinib or cerdulatinib was added into the culture and live cell number was counted daily for 7 days. The results shown are the mean±SE of 4 replicate experiments. Open circle=dimethylsulfoxide ("DMSO"); closed circle=ibrutinib ("IBR"); triangle=cerdulatinib ("Cerd").

It was observed that the growth of WT BTK-transfected TMD8 cells was similarly inhibited by both ibrutinib and cerdulatinib at 250 nM (FIG. 4). However, $BTK^{C481S}$-transfected cells were less sensitive to ibrutinib, as expected (FIG. 5). Meanwhile, growth of these cells was effectively blocked by cerdulatinib, similar to the block observed in WT BTK cells.

Example 5: Case Studies for Patients with Follicular Lymphoma

CASE STUDY 1 (Patient 1): The patient was a 71 year old Caucasian female with transformed follicular 3B lymphome (MYC/BCL2/BCL6 positive by IHC). The tumor was CD20+, CD10−, BCL2 (strong), cMYC (50%), and Ki67 (80%).

The patient's prior therapies included: R-CHOP (Rituximab; Cyclophosphamide; Doxorubicin hydrochloride; Oncovin; Prednisone) (November 2013-February 2014). The patient relapsed in February 2015. The patient began cerdulatinib 65 mg by mouth once daily ("PO QD") in March 2015.

The following was observed: Steady state $C_{min}$-$C_{max}$ was 0.73-1.74 µM; % Inhibition BCR signaling was 100%; % Inhibition IL2, IL4, IL6 signaling was 60-100%; and % Inhibition GM-CSF was ~20%. The patient showed partial response to cerdulatinib (69%) after 2 cycles.

Patient 1 progressed in August 2015. Patient 1 relapsed following 5 cycles of therapy.

CASE STUDY 2 (Patient 2): The patient was a 71 year old Caucasian female with Follicular Lymphoma.

The patient's prior therapies included: Chlorambucil (1998; CR), Fludarabine/Rituxan (1999-2000; CR), and Avastin/Rituxan (March 2011-January 2012). Patient 2 relapsed in September 2014. Patient 2 began cerdulatinib 45 mg PO QD in October 2014, and the dose reduced to 30 mg due to fatigue.

The following was observed: Steady state $C_{min}$-$C_{max}$ was 0.25-0.63 µM. % Inhibition BCR signaling; 90% for pSYK Y525/525, 0% for pERK Y204; % Inhibition IL2, IL4, IL6 signaling was 60-100%; % Inhibition GM-CSF was 0%; partial response to cerdulatinib (56%) after 2 cycles and 76% nodal reduction after one year on therapy.

Patient 2 remains on the drug.

CASE STUDY 3 (Patient 3): The patient was a 79 year old Caucasian male with Follicular Lymphoma. The patient's tumor bears a S86A mutation in STAT.

The patient's prior therapies: R-CVP (Rituximab; Cyclophosphamide; Vincristine; Prednisolone) (2006-2007), R-maintenance (2006-2008), BR (Bendamustine; Rituximab) (May 2013-September 2013), Ibrutinib (October 2013-April 2014), R-CHOP (December 2013-April 2014). Patient 3 relapsed in May 2014. Patient 3 was given cerdulatinib 15 mg by mouth twice daily ("PO BID") June 2014. Stable disease was observed in Patient 3 for 6 months on cerdulatinib (20% nodal reduction).

These case studies show that cerdulatinib has been well-tolerated to date and has promising activity in heavily pre-treated patients having follicular lymphoma. Responses have been seen in other Non-Hodgkin's Lymphomas (NHL).

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of treating a follicular lymphoma in a human patient in need thereof, comprising administering to the patient about 15 mg or about 30 mg of cerdulatinib or a pharmaceutically acceptable salt thereof twice daily, or about 30 mg of cerdulatinib or a pharmaceutically acceptable salt thereof once daily, wherein the cerdulatinib is administered as a monotherapy and not administered in combination with another anticancer drug therapy.

2. The method of claim 1, wherein the follicular lymphoma is relapsed or refractory.

3. The method of claim 1, wherein the follicular lymphoma is transformed follicular lymphoma.

4. The method of claim 1, wherein the patient was previously administered a drug selected from the group consisting of an alkylating agent, an anti-CD20 antibody, a BCL-2 inhibitor, a BTK inhibitor, a P13Kδ inhibitor, a platinum-based drug, an antimetabolite, an anthracycline, a BCR pathway inhibitor, and another chemotherapeutic agent used for treating a follicular lymphoma.

5. The method of claim 1, wherein the patient was previously administered a drug selected from the group consisting of venetoclax, rituximab, ibrutinib, idelalisib, and fludarabine.

6. The method of claim 1, wherein the cerdulatinib is administered in a pharmaceutical composition further comprising a pharmaceutically acceptable excipient or carrier.

7. The method of claim 1, wherein the patient has a mutation linked to relapse or a resistance to a drug for treating a follicular lymphoma, wherein the mutation is a del17p mutation, a P53 mutation, an ATM mutation, a STAT mutation, a STAT 6 mutation, a C481S STAT6 mutation, a mutation associated with the NOTCH pathway, a mutation associated with the Cadherin pathway, or a combination thereof.

8. The method of claim 1, wherein the patient was previously administered a drug selected from the group consisting of venetoclax, rituximab, ibrutinib, idelalisib, fludarabine, R-CHOP (Rituximab; Cyclophosphamide; Doxorubicin hydrochloride; Oncovin (vincristine); Prednisone, R-CVP (Rituximab; Cyclophosphamide; Vincristine; Prednisone), bevacizumab, a combination of fludarabine and rituximab, a combination of bendamustine and rituximab, and a combination of bevacizumab and rituximab.

9. The method of claim 1, wherein the patient is 60 years or older and relapsed after a first line cancer therapy.

10. The method of claim 1, wherein the patient was previously administered a once daily a dose of about 45 mg of cerdulatinib or a pharmaceutically acceptable salt thereof and showed fatigue.